US011123064B2

(12) United States Patent
Chen et al.

(10) Patent No.: US 11,123,064 B2
(45) Date of Patent: Sep. 21, 2021

(54) TISSUE CLOSURE DEVICE

(71) Applicant: TOUCHSTONE INTERNATIONAL MEDICAL SCIENCE CO.,LTD, Suzhou (CN)

(72) Inventors: Wangdong Chen, Suzhou (CN); Teng Shan, Suzhou (CN); Tuo Shu, Suzhou (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 444 days.

(21) Appl. No.: 16/323,771

(22) PCT Filed: Dec. 26, 2016

(86) PCT No.: PCT/CN2016/112079
§ 371 (c)(1),
(2) Date: Feb. 6, 2019

(87) PCT Pub. No.: WO2018/028118
PCT Pub. Date: Feb. 15, 2018

(65) Prior Publication Data
US 2019/0167265 A1 Jun. 6, 2019

(30) Foreign Application Priority Data

Aug. 8, 2016 (CN) .......................... 201610642770.5
Aug. 8, 2016 (CN) .......................... 201610645003.X
Aug. 8, 2016 (CN) .......................... 201620851420.5

(51) Int. Cl.
*A61B 17/122* (2006.01)
*A61B 17/128* (2006.01)
(Continued)

(52) U.S. Cl.
CPC .......... *A61B 17/072* (2013.01); *A61B 17/115* (2013.01); *A61B 17/1114* (2013.01);
(Continued)

(58) Field of Classification Search
CPC ..... A61B 17/12; A61B 17/122; A61B 17/128; A61B 17/1285; A61B 17/1114;
(Continued)

(56) References Cited

FOREIGN PATENT DOCUMENTS

| CN | 104434244 A | 3/2015 |
|---|---|---|
| CN | 204394620 U | 6/2015 |

(Continued)

OTHER PUBLICATIONS

International Search Report for PCT /CN2016/112079 dated May 3, 2017 and its English translation provided by WIPO.
Written Opinion for PCT /CN2016/112079 dated May 3, 2017 and its English translation provided by WIPO.
International Preliminary Report on Patentability (IPRP) dated Feb. 12, 2019.
(Continued)

*Primary Examiner* — Diane D Yabut
*Assistant Examiner* — Christian D Knauss
(74) *Attorney, Agent, or Firm* — Ladas & Parry, LLP

(57) ABSTRACT

The present invention provides a tissue closure device, comprising: a first and a second clamping base which form a cavity there between for accommodating a tubular tissue; and a pouch assembly comprises: a tying band provided with a first free end and a second free end; a first tying band buckle which is arranged adjacent to the first free end in an initial state; a second tying band buckle arranged adjacent to the second free end in an initial state, wherein the second tying band buckle is buckled with the first tying band buckle after the first and the second clamping base are closed; and a first driving mechanism which enables the first and the second tying band buckle to move synchronously after the first and the second tying band buckle are buckled and then cooperate with the tying band to gather the tubular tissue into a pouch.

16 Claims, 13 Drawing Sheets

(51) Int. Cl.
  *A61B 17/072* (2006.01)
  *A61B 17/12* (2006.01)
  *A61B 17/115* (2006.01)
  *A61B 17/3209* (2006.01)
  *A61B 17/11* (2006.01)
  *A61B 17/00* (2006.01)
  *A61B 17/064* (2006.01)

(52) U.S. Cl.
  CPC ...... *A61B 17/122* (2013.01); *A61B 17/12013* (2013.01); *A61B 17/1285* (2013.01); *A61B 17/3209* (2013.01); *A61B 2017/00818* (2013.01); *A61B 2017/0647* (2013.01); *A61B 2017/07214* (2013.01); *A61B 2017/07285* (2013.01)

(58) Field of Classification Search
  CPC .......... A61B 17/3209; A61B 17/12009; A61B 17/12013; A61B 17/12018; A61B 2017/00818; A61B 2017/1125; A61F 5/0083; A61F 5/0086
  See application file for complete search history.

(56) References Cited

FOREIGN PATENT DOCUMENTS

| | | |
|---|---|---|
| CN | 204971431 U | 1/2016 |
| CN | 105997174 A | 10/2016 |
| CN | 106137290 A | 11/2016 |
| CN | 206120383 U | 4/2017 |
| CN | 206120384 U | 4/2017 |
| WO | WO-2012126477 A1 * | 9/2012 ......... A61B 17/1285 |

OTHER PUBLICATIONS

First Office action, search report dated Dec. 5, 2017 and translation for related Chinese Application 201610642770.5 (CN 105997174 A) provided by Google Translate.
Second Office action dated Jul. 16, 2018 and translation for related Chinese Application 201610645003.X (CN106137290) provided by Google Translate.
Third Office action and translation for related Chinese Application 201610645003.X (CN106137290) provided by Google Translate.
First Office action and search report dated Dec. 5, 2017 and translation for related Chinese Application 201610645003.X (CN 106137290 A) provided by Google Translate.

* cited by examiner

TISSUE CLOSURE DEVICE

CROSS-REFERENCE TO RELATED APPLICATIONS

This application is the U.S. national phase of PCT/CN2016/112079 filed on Dec. 26, 2016, which claims the priority of to the Chinese Patent Application No. 201610645003.X, titled "Tissue Closure Device" and filed on Aug. 8, 2016, the Chinese patent application No. 201610642770.5, titled "Tissue Closure Device" and filed on Aug. 8, 2016, and the Chinese patent application No. 201620851420.5, titled "Tissue Closure Unit and Tissue Closure Device" and filed on Aug. 8, 2016, the disclosures of which are incorporated herein by reference in their entireties.

TECHNICAL FIELD

The present invention relates to the technical field of medical instruments, and particularly to a tissue closure device.

BACKGROUND

In the existing digestive tract anastomosis surgery, a linear stapler or arcuate stapler is generally used firstly for performing multi-angle resection and anastomosis on human tubular tissues, and then connection and anastomosis are performed on the divided tissues by using a tubular stapler.

However, after the human tubular tissues are subjected to resection and anastomosis with the linear stapler or arcuate stapler, a cross-staple phenomenon will appear due to linear staple lines on the anastomosis stoma, especially, due to the limitations of both a human pelvic floor operation space and the swing angle of the linear stapler when the surgery is performed at a lower rectum position. As a result, "dog ears" will appear when the tubular stapler is used to perform anastomosis on tissues. Thus, the surgery has a higher risk of stoma fistula, and the surgery cost is relatively high.

SUMMARY

The object of the present invention is to provide a tissue closure device which may reduce risks and is convenient to use.

In order to achieve the above purpose, the present invention provides a tissue closure device, comprising: a first clamping base and a second clamping base which may be opened and closed oppositely and form a cavity therebetween for accommodating a tubular tissue when being closed; and a pouch assembly arranged to cooperate with the first clamping base and the second clamping base, wherein the pouch assembly comprises a tying band which extends along the side, facing the cavity, of each of the first clamping base and the second clamping base, and is provided with a first free end located at the distal end of the first clamping base and a second free end located at the distal end of the second clamping base; a first tying band buckle which is slidably arranged on the tying band in a penetrating manner and arranged adjacent to the first free end in an initial state; a second tying band buckle which is slidably arranged on the tying band in a penetrating manner and arranged adjacent to the second free end in an initial state, wherein the second tying band buckle is opposite to the first tying band buckle and buckled with the first tying band buckle after the tubular tissue is accommodated in the cavity and the first clamping base and the second clamping base are closed; and a first driving mechanism which enables the first tying band buckle and the second tying band buckle to move synchronously relative to the tying band after the first tying band buckle and the second tying band buckle are buckled and then cooperate with the tying band to gather the tubular tissue into a pouch.

The present invention has the following beneficial effects: the tubular tissue is formed into a bundled pouch with a gathered center through the tissue closure device, so that the risks of "dog ears" and stoma fistula arising from subsequent anastomosis through a tubular stapler are reduced. At the same time, the tissue closure device is simple in operation and convenient to use and reduces the surgery cost.

DETAILED DESCRIPTION

Figure 1:
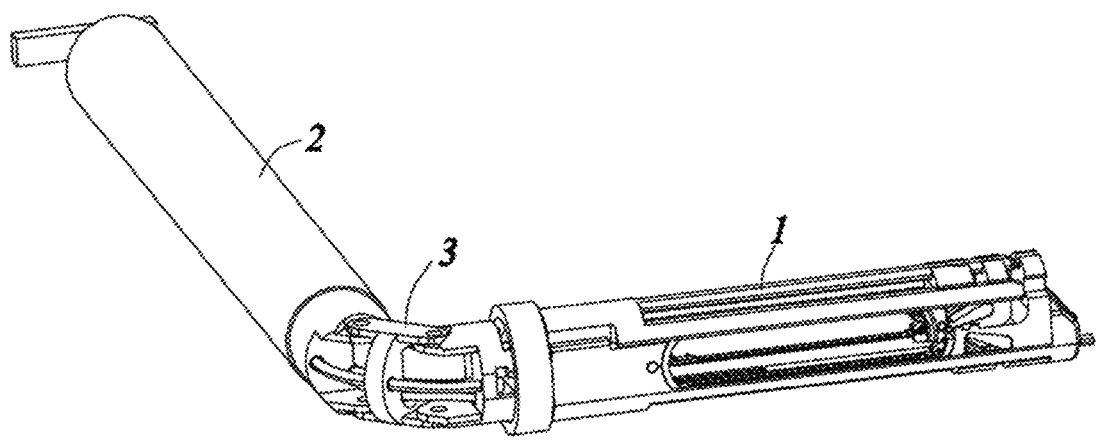
FIG. 1 is an elevation view of a tissue closure device in one embodiment of the present invention.
Figure 2:
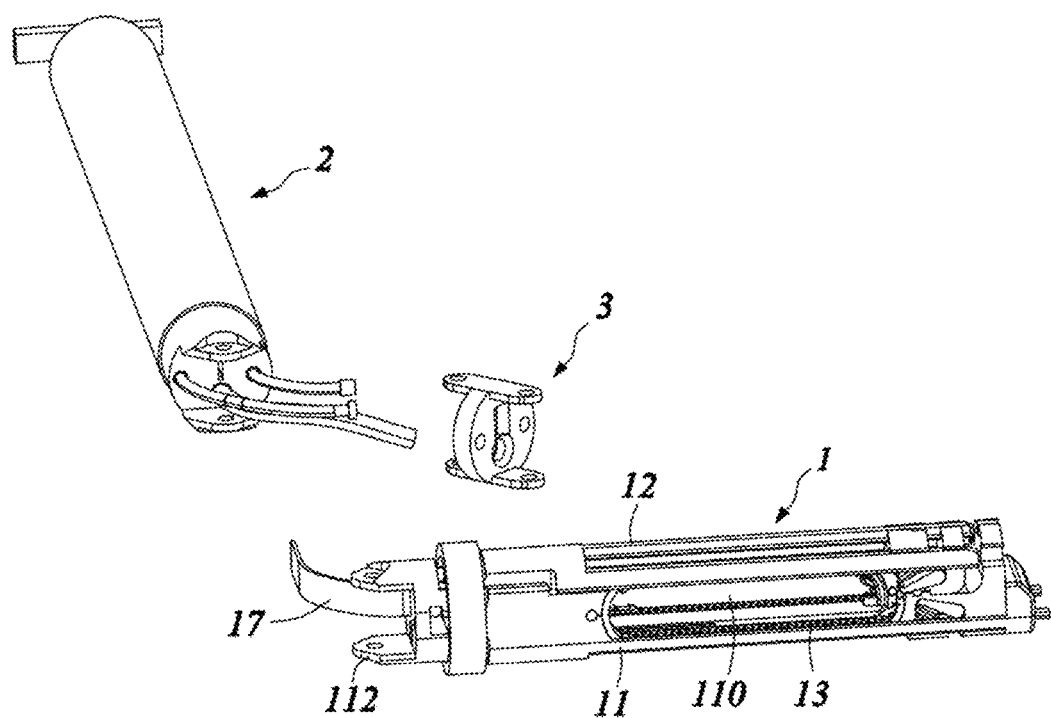
FIG. 2 is a partial exploded view of the tissue closure device shown in FIG. 1.
Figure 3:
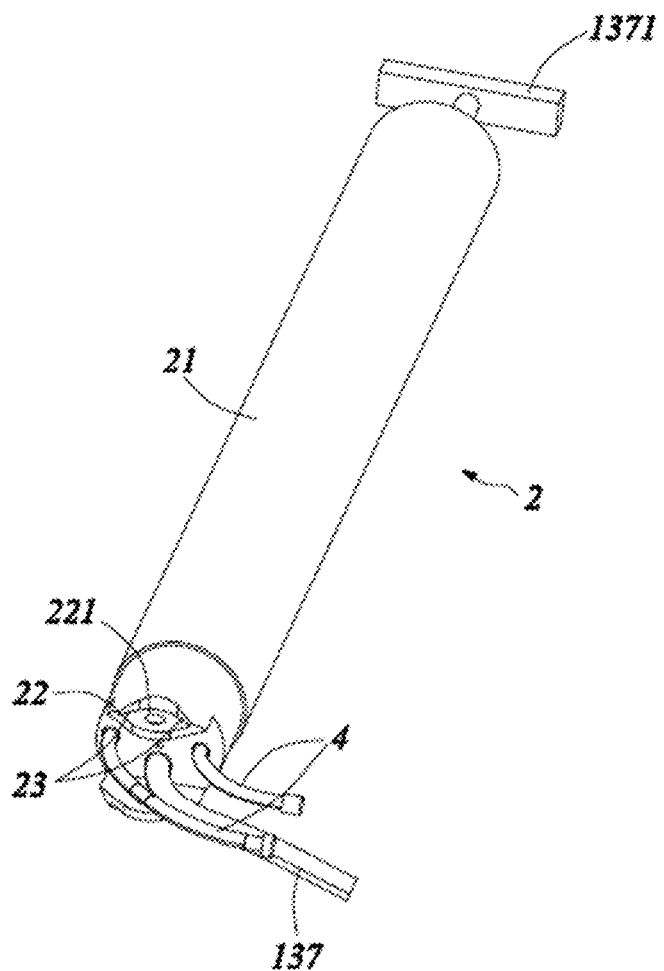
FIG. 3 is a stereoscopic diagram of an instrument body of the tissue closure device shown in FIG. 1.
Figure 4:
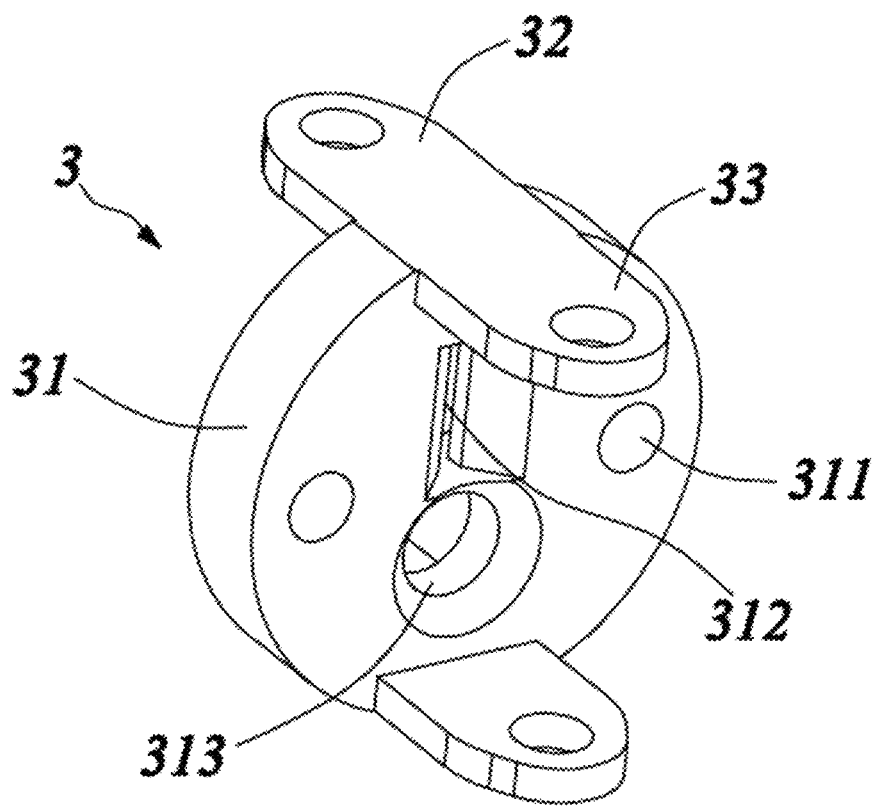
FIG. 4 is a stereoscopic diagram of an adapter of the tissue closure device shown in FIG. 1.
Figure 5:
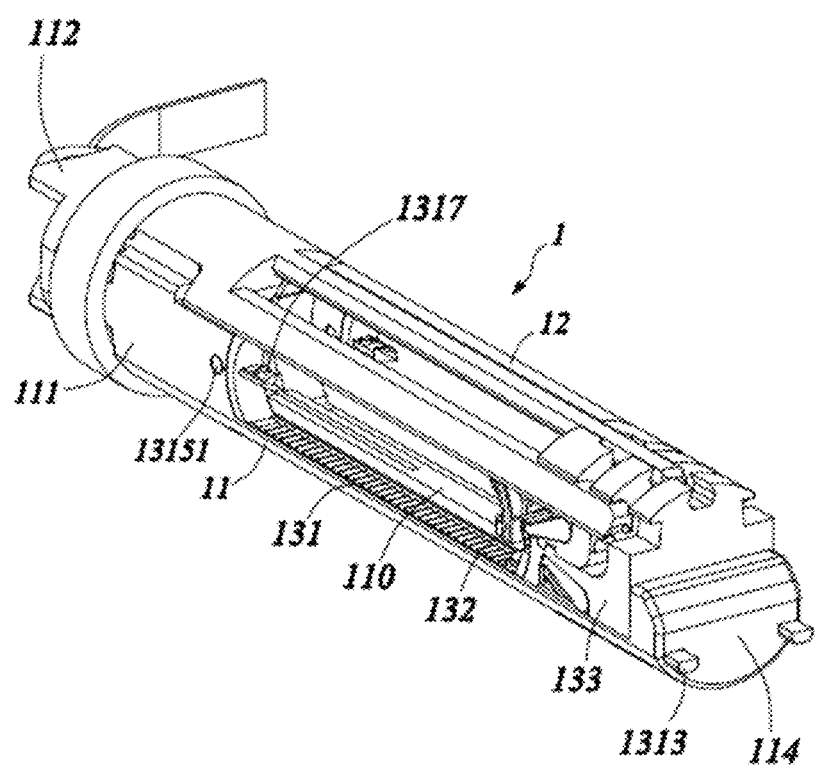
FIG. 5 is a stereoscopic diagram of a tissue closure unit of the tissue closure device shown in FIG. 1.
Figure 6:
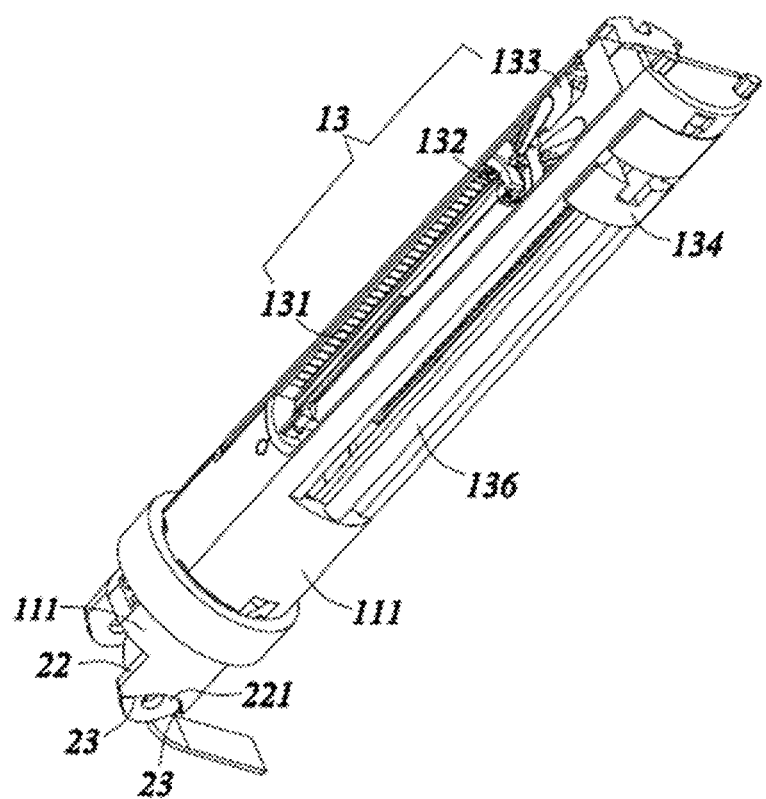
FIG. 6 is a stereoscopic diagram of the tissue closure unit in FIG. 5 from another perspective.

The present invention will be described in detail below with reference to specific embodiments shown in the accompanying drawings. However, these embodiments are not intended to limit the present invention, and changes of structures, methods or functions, made by an ordinary person skilled in the art according to these embodiments are included within the scope of protection of the present invention.

In order to clearly express the position and direction described in the present invention, reference is made to an instrument operator, the end close to the operator is a proximal end, and the end away from the operator is a distal end.

As shown in FIGS. 1-14, the present invention discloses an embodiment of a medical instrument. The medical instrument may be used in a digestive tract anastomosis surgery, and is specifically a tissue closure device which comprises a tissue closure unit 1, an instrument body 2 and an adapter 3 connected between the tissue closure unit 1 and the instrument body 2. The tissue closure unit 1 is arranged at the distal end. The instrument body 2 is arranged at the proximal end. The adapter 3 is connected between the tissue closure unit 1 and the instrument body 2.

In conjunction with FIGS. 2 and 5-11, the tissue closure unit 1 comprises a first clamping base 11 and a second clamping base 12 which may be opened and closed oppositely, and a pouch assembly 13 arranged to cooperate with the first clamping base 11 and the second clamping base 12.

The first clamping base 11 is provided with a first base portion 111 rotationally cooperating with the second clamping base 12, a lug 112 protruding from the first base portion 111 towards the adapter 3, and a first clamping portion 113 extending from the first base portion 111 towards the distal end.

The second clamping base 12 is provided with a second base portion 121 cooperating with the first base portion 111, and a second clamping portion 122 extending from the second base portion 121 towards the distal end. When the first clamping base 11 and the second clamping base 12 are closed, a cavity 110 for accommodating a tubular tissue is formed between the first clamping portion 113 and the second clamping portion 122.

With reference to FIGS. 7-11, a U-shaped groove is formed at the side, close to the lug 112, of the first base portion 111, and the side, connected to the first clamping portion 113, of the first base portion 111 is formed as a support portion 1111 for supporting the second base portion 121. An accommodation portion 1112 open towards the second clamping base 12 is arranged between the U-shaped groove and the support portion 1111. The U-shaped groove comprises a first groove 1113 open towards the second base portion 121, a second groove 1114 spaced from the first groove 1113 and close to the lug 112, and a communication groove 1115 connected to the first groove 1113 and the second groove 1114. A blocking portion 1116 is formed between the first groove 1113 and the second groove 1114.

A rotating shaft 1211 is arranged at the end, close to the adapter 3, of the second base portion 121, and the side, connected to the second clamping portion 122, of the second base portion 121 is formed as an abutting portion 1212 which is abutted against the support portion 1111 during closure. An intermediate portion 1213 is connected between the rotating shaft 1211 and the abutting portion 1212.

During mounting, the rotating shaft 1211 passes through the first groove 1113 and the communication groove 1115, stretches into and is positioned in the second groove 1114. The intermediate portion 1213 is accommodated in the accommodation portion 1112. An elastic element 14 is arranged between the intermediate portion 1213 and the bottom wall of the accommodation portion 1112 for abutting against an inner wall surface of the intermediate portion 1213 when the second clamping base 12 is opened, thereby keeping an open state of the second clamping base 12.

The overall outer diameter obtained after the lug 112, a position, adjacent to the lug 112, of the first base portion 111, and a position, adjacent to the rotating shaft 1211, of the intermediate portion 1213 of the second base portion 121 are closed is smaller than the outer diameter of the other portions of the first base portion 111 and the second portion base 121. The tissue closure unit 1 further comprises a driving ring 15 sleeve portions, with the relatively small outer diameter, of the first base portion 111 and the second base portion 121. A push-pull element (not shown) which may drive the driving ring 15 to move axially along the tissue closure unit 1 is arranged on the instrument body 2. When the push-pull element drives the driving ring 15 to move towards the proximal end, the second base portion 121 disengages from the driving ring 15, and is pushed up through the elastic element 14 to enable the second clamping base 12 to be opened outwards. When the driving ring 15 moves towards the distal end, the driving ring 15 gradually retracts the second clamping base 12, so that the second clamping base 12 moves towards the first clamping base 11 and thus the two clamping bases are closed.

The first clamping portion 113 is provided with a sliding portion connected to the first base portion 111 and a stopper 114 fixed to the distal end of the sliding portion. The second clamping portion 122 is also provided with a sliding portion corresponding to the sliding portion of the first base portion 111.

In this embodiment, each of the sliding portions of the first clamping portion 113 and the second sliding portion 122 is provided with a first sliding rod 115 and a second sliding rod 116 which are arranged at an interval along the radial direction, and a third sliding rod 117 located between the first sliding rod 115 and the second sliding rod 116.

A tying band groove 1151 is recessed at the side, facing the cavity 110, of each of the first sliding rod 115 and the second sliding rod 116. A positioning portion 1117 for positioning the pouch assembly 13 is arranged at a position, corresponding to the tying band groove 1151, of the first base portion 111. On the second clamping portion 122, a positioning convex block 1221 protruding into the tying band groove 1151 is arranged at the distal end, at the tying band groove 1151, of each of the first sliding rod 115 and the second sliding rod 116. On the first clamping portion 113, a hole 1141 corresponding to the tying band groove 1151 is arranged on the stopper 114.

At the outer side, away from the cavity 110, of the third sliding rod 117, one cooperation hole 118 is arranged on each of the first base portion 111 and the stopper 114, and these two cooperation holes axially correspond to each other. In addition, each of the first base portion 111 and the second base portion 121 is further provided with an axial knife feeding groove 119 between the first sliding rod 115 and the second sliding rod 116. The knife feeding groove 119 extends to the proximal end of the first clamping portion 113 and is communicated with the cavity 110.

In conjunction with FIGS. 5-8, the pouch assembly 13 comprises a tying band 131 extending along the side, facing the cavity 110, of each of the first clamping base 11 and the second clamping base 12, a tying band buckle 132 slidably arranged on the tying band 131 in a penetrating manner, and a first driving mechanism 133 for enabling the tying band buckle 132 to move relative to the tying band 131. The cavity 110 for accommodating the tubular tissue may be actually regarded as being formed between the tying band 131 and the tying band buckle 132.

In this embodiment, to be specific, the tying band 131 comprises a first tying band 1311 and a second tying band 1312 which are arranged at an interval side by side along the radial direction and correspond to the first sliding rod 115 and the second sliding rod 116 respectively.

Each tying band 131 is bent to be U-shaped and is provided with a first free end 1313 fixed to the distal end of the first clamping base 11, a second free end 1314 fixed to the distal end of the second clamping base 12, a connection portion 1315 fixed to the proximal end of the first clamping base 11, and main body portions 1316 connected between the first free end 1313 as well as the second free end 1314 and the connection portion 1315. The tying band buckle 132 may move from the distal end to the connection portion 1315 along the main body portion 1316 so as to gradually shrink the cavity 110 and tighten the tubular tissue.

The connection portion 1315 is fixed to the positioning portion 1117 of the first base portion 111 through a T-shaped positioning structure 13151 connected to the outer side of the connection portion 1315.

The main body portion 1316 is embedded into the tying band groove 1151, and a first ratchet 13160 for unidirectionally and cooperatively sliding with the tying band buckle 132 is arranged at the side, facing the cavity 110, of the main body portion.

In addition, each of the tying bands 131 is further provided with a thorn 1317 protruding from the connection portion 1315 and/or a position, adjacent to the connection portion 1315, of the main body portion 1316, into the cavity 110. The thorn 1317 is used to insert into and fix the tubular tissue.

Figure 7:
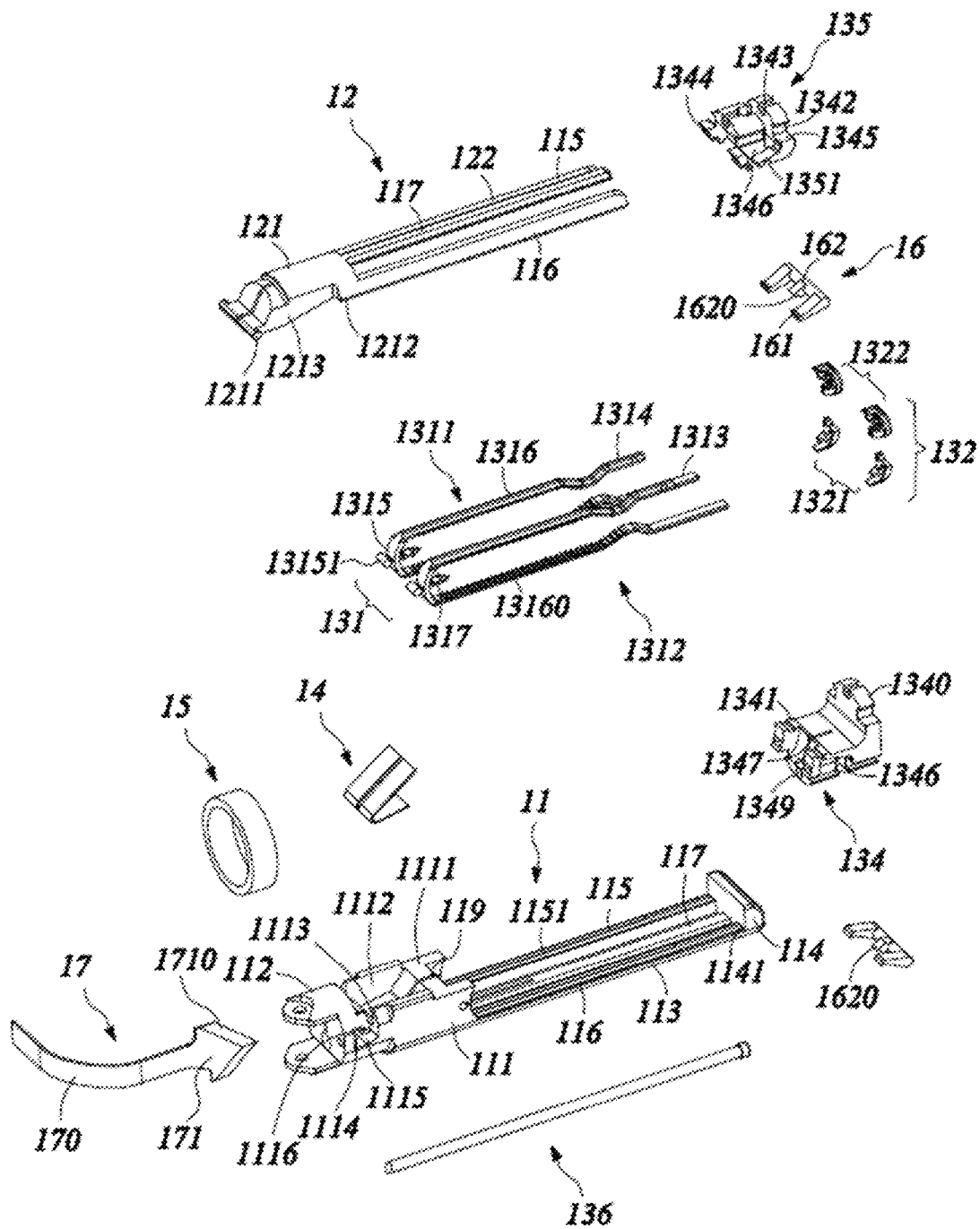
FIG. 7 is a stereoscopic exploded view of the tissue closure unit in FIG. 5.
Figure 8:
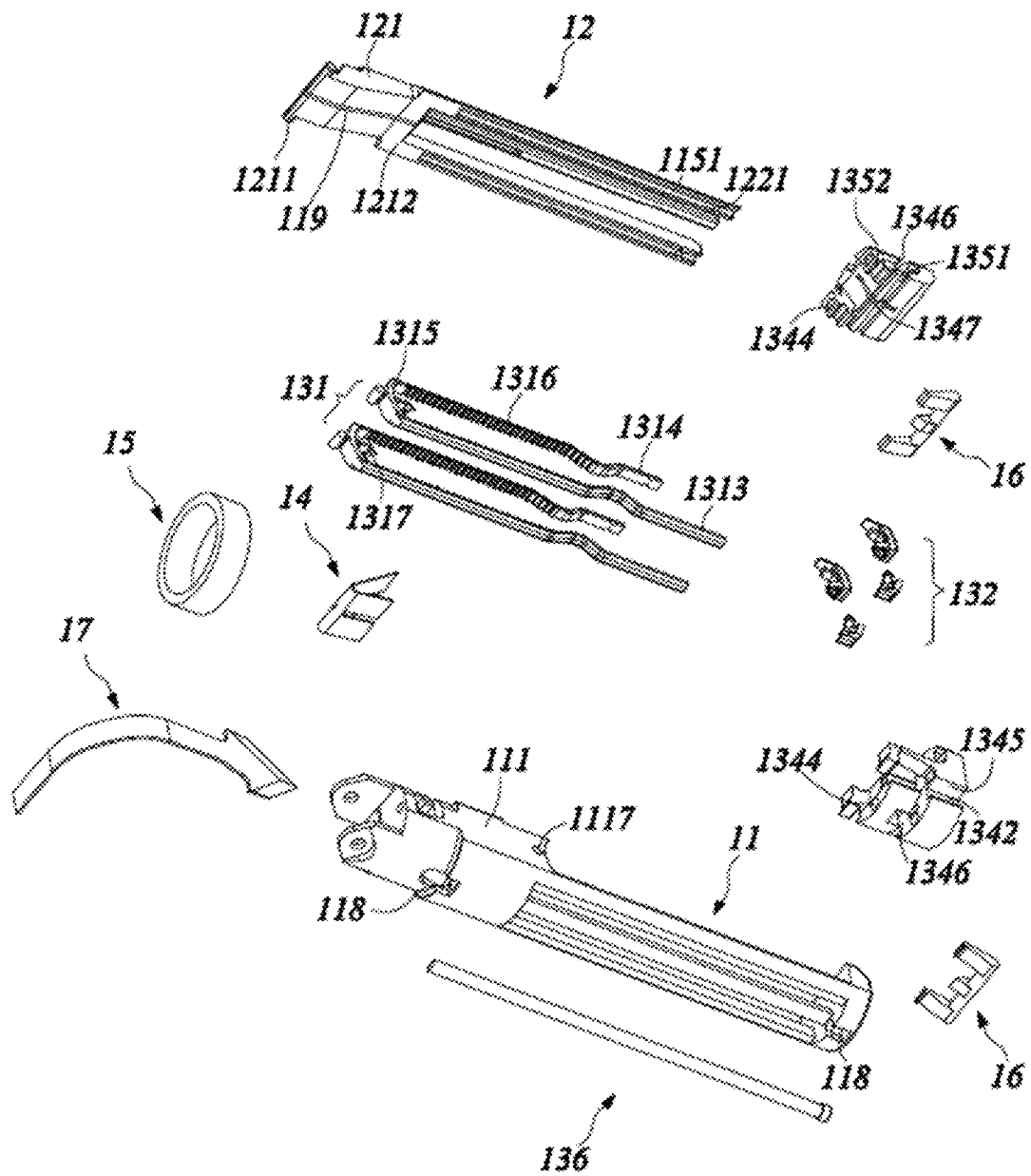
FIG. 8 is a view of FIG. 7 from another perspective.
Figure 9:
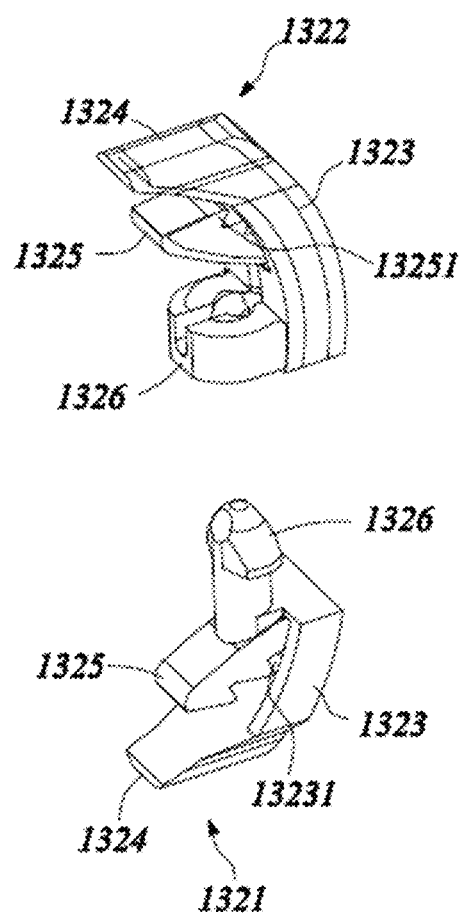
FIG. 9 is a stereoscopic diagram of a tying band buckle in the tissue closure unit shown in FIG. 5.
Figure 10:
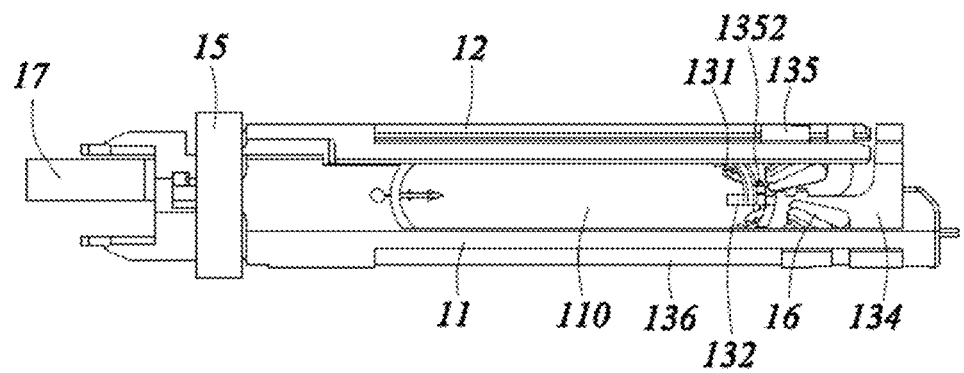
FIG. 10 is a side view of the tissue closure unit shown in FIG. 5 in an initial state.
Figure 11:
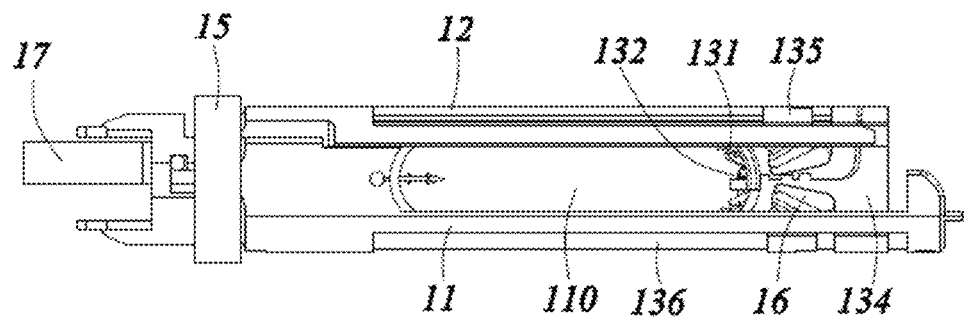
FIG. 11 is a side view of the tissue closure unit shown in FIG. 5 when the tying band buckles are mutually buckled.

As shown in FIGS. 7 and 8, in this embodiment, the thorn 1317 protrudes from the proximal end to the distal end at the inner side of the connection portion 1315. One thorn 1317 is arranged at an intermediate position of the connection portion 1315 of each tying band 131 in a protruding manner. Of course, as another preferred embodiment of the present invention, there may also be at least one pair of thorns 1317 protruding from the inner side of the connection portion 1315 into the cavity 110. The at least one pair of thorns 1317 is arranged at an interval at the inner side of the connection portion 1315 and is in central symmetry about the connection portion 1315. Moreover, in this case, no thorn 1317 may be arranged in the center position of the connection portion 1315 in a protruding manner, thereby facilitating the insertion of the staple head (not shown) of the stapler.

Figure 12:
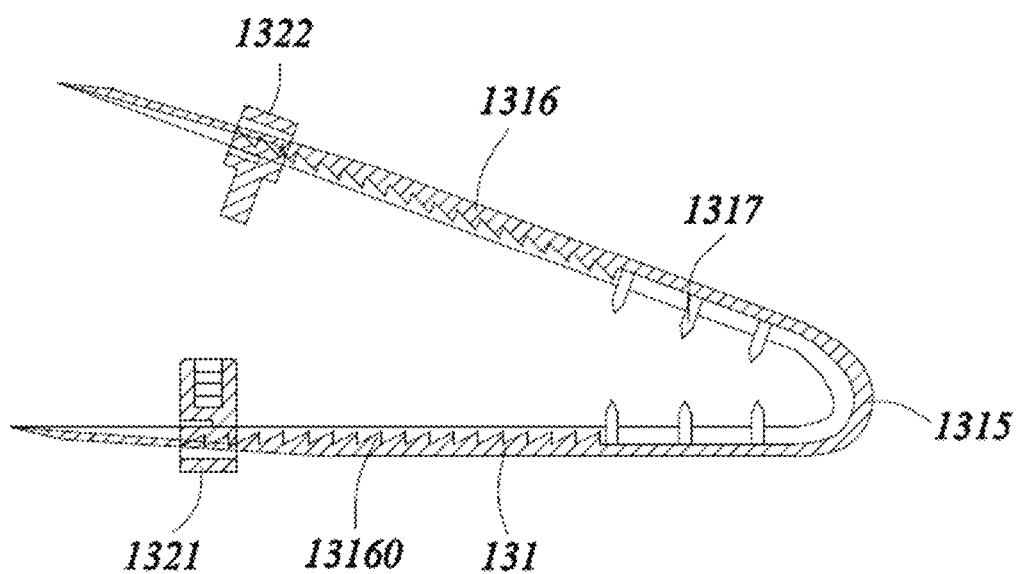
FIG. 12 is a stereoscopic diagram of a tying band and a tying band buckle in another preferred embodiment of the present invention.

As shown in FIG. 12, in still another preferred embodiment of the present invention, the thorn 1317 is arranged on the main body portion 1316. Each of the main body portions 1316 connected to two sides of the connection portion 1315 is provided with the thorn 1317 protruding into the cavity 110, so that both tubular tissues adjacent to the two main body portions 1316 may be positioned. In this embodiment, the thorns 1317 on the main body portions 1316 at two sides of the connection portion 1315 extend oppositely. A gap is formed between the thorns 1317 on the two main body portions 1316 for facilitating continuously gathering the tubular tissue towards the proximal end. Of course, the thorn 1317 may also extends obliquely as long as it is capable of piercing into the tubular tissue for positioning.

With reference to FIGS. 7-11, the tying band buckle 132 comprises a first tying band buckle 1321 and a second tying band buckle 1322 which are slidably arranged on the two main body portions 1316 respectively of each tying band 131. The first tying buckle tape 1321 is adjacent to the first free end 1313 in an initial state. The second tying band buckle 1322 is adjacent to the second free end 1314 in an initial state.

On each tying band 131, the second tying band buckle 1322 is opposite to the first tying band buckle 1321 and buckled with the first tying band buckle 1321 after the tubular tissue (not shown) is accommodated in the cavity 110 and the first clamping base 11 and the second clamping base 12 are closed. In this embodiment, the first driving mechanism 133 drives the first tying band buckle 1321 and the second tying band buckle 1322 to move synchronously from the distal end to the proximal end along the tying band 131 after the first tying band buckle 1321 and the second tying band buckle 1322 are buckled and then cooperate with the tying band 131 to gather the tubular tissue into a pouch.

With reference to FIGS. 7-11, in this embodiment, each of the tying band buckles 132 is provided with a sleeve portion 1323 slidably sleeving the main body portion 1316 of the tying band 131 in a penetrating manner, a pushing portion 1324 and a restriction portion 1325 which are connected to the sleeve portion 1323 and located at two sides of the tying band 131 respectively, and a positioning buckle 1326.

A portion, between the pushing portion 1324 and the restriction portion 1325, of the sleeve portion 1323 is provided with a connecting hole 13231 for allowing the tying band 131 to pass through and enabling the tying band buckle 132 to slide along the tying band 131. The position, cooperating with the sleeve portion 1323, of the main body portion 1316 of the tying band 131 disengages from the tying band groove 1151 and stretches into the cavity 110.

The pushing portion 1324 is formed by protruding towards the proximal end from the end of the sleeve portion 1323 facing the tying band groove 1151, stretches into the tying band groove 1151, and pushes the main body portion 1316 of the tying band 131 out of the tying band groove 1151 for facilitating movement in the process that the tying band buckle 132 slides towards the proximal end.

The restriction portion 1325 is used for unidirectionally cooperating with the first ratchet 13160 on the tying band 131, and thus is provided with a second ratchet 13251 for unidirectionally cooperating with the first ratchet 13160, such that the tying band buckle 132 may only move towards the proximal end along the tying band 131.

The positioning buckle 1326 on the first tying band buckle 1321 is a protruding column protruding from the restriction portion 1325 into the cavity 110. A positioning bump with a relatively large outer diameter is formed at the tail end of the protruding column. The positioning buckle 1326 on the second tying band buckle 1322 is a protruding ring which protrudes from the tail end, stretching into the cavity 110, of the sleeve portion 1323 towards the proximal end. Of course, the positioning buckles 1326 on the first tying band buckle 1321 and the second tying band buckle 1322 may be substituted by each other, and the effect of buckling the first tying band buckle 1321 and the second tying band buckle 1322 for positioning may be achieved too.

Figure 13:
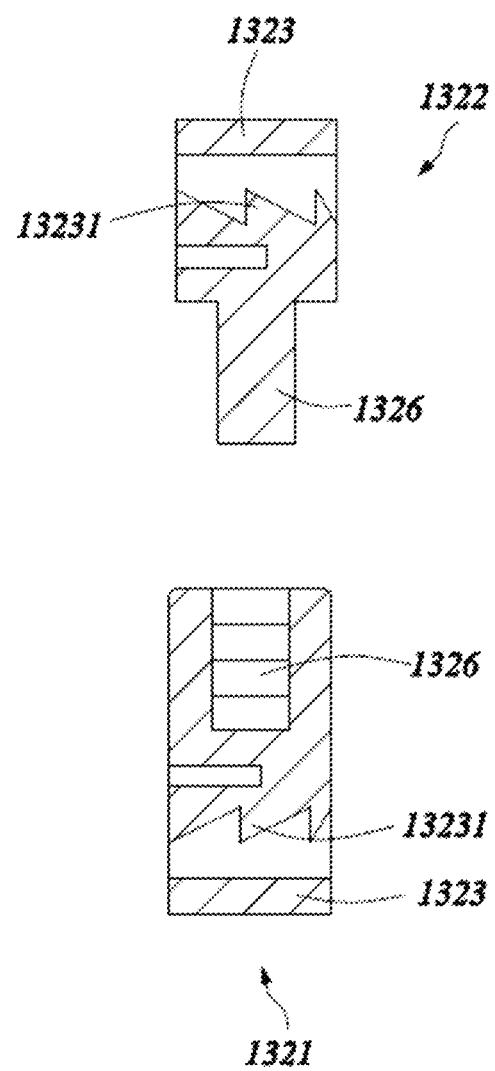
FIG. 13 is a stereoscopic diagram of the tying band in FIG. 12.

As another preferred embodiment of the present invention, with reference to FIGS. 12 and 13, each of the first tying band buckle 1321 and the second tying band buckle 1322 may only be provided with a sleeve portion 1323 slidably sleeving the tying band 131, and a positioning buckle 1326 connected to the sleeve portion 1323. A second ratchet 13251 for unidirectionally cooperating with the first ratchet 13160 on the tying band 131 is arranged at the inner side of the sleeve portion 1323. The positioning buckles 1326 are a positioning hole and a protruding column arranged at opposite sides of the first tying band buckle 1321 and the second tying band buckle 1322 respectively, and the purpose of the present invention may be achieved too.

With reference to FIGS. 1-11, in this embodiment, the first driving mechanism 133 comprises a first sliding block 134 and a second sliding block 135 respectively arranged on the first clamping base 11 and the second clamping base 12 in a sliding manner along the axial direction, and a transmission mechanism 136. The transmission mechanism 136 cooperates with the first sliding block 134 to drive the tying band buckle 132 to move along the tying band 131. Two groups of tying bands 131 and tying band buckles 132 share the first sliding block 134 and the second sliding block 135.

The first sliding block 134 is abutted against the side, facing the first free end 1313, of the first tying band buckle 1321. The second sliding block 135 is abutted against the side, facing the second free end 1314, of the second tying band buckle 1322. A positioning convex block 1341 and a positioning groove 1351 which are mutually positioned are arranged at opposite sides of the first sliding block 134 and the second sliding block 135 respectively.

The transmission mechanism 136 is arranged to cooperate with the first sliding block 134. When the tissue closure unit 1 is in an initial state, the first sliding block 134 and the second sliding block 135 are respectively located at the distal ends of the first clamping base 11 and the second clamping base 12, and the first tying band buckle 1321 and the second tying band buckle 1322 are staggered. A make-way groove 1352 is arranged at the position, corresponding to the positioning buckle 1326 of the first tying band buckle 1321, on the second sliding block 135. At this time, the positioning buckle 1326 of the first tying band buckle 1321 stretches into the make-way groove 1352, and the positioning buckle 1326 of the second tying band buckle 1322 is located at the outer side of the proximal end of the first tying band buckle 1321.

After the first clamping base 11 and the second clamping base 12 are oppositely opened to accommodate the tubular tissue in the cavity 110, the transmission mechanism 136 drives the first sliding block 134 and thus pushes the first tying band buckle 1321 to move towards the proximal end along the tying band 131 to a first position. Then, the first clamping base 11 and the second clamping base 12 are closed, and at this position, the first tying band buckle 1321 and the second tying band buckle 1322 are buckled through the positioning buckle 1326, and the first sliding block 134 and the second sliding block 135 are also positioned through the cooperation between the positioning convex block 1341 and the positioning groove 1351. Finally, the transmission mechanism 136 continuously drives the first sliding block 134 and then drives the second sliding block 135 to move towards the proximal end at the same time, so that the first tying band buckle 1321 and the second tying band buckle 1322 synchronously move from the distal end to the proximal end along the tying band 131 and thus the tubular tissue is gathered towards the proximal end to form a pouch.

Further, in order to guarantee that the first sliding block 134 smoothly pushes the second sliding block 135 and the tying band buckle 132 towards the proximal end, a convex wall 1340 protruding towards the second sliding block 135 is arranged at the distal end of the first sliding block 134, so that in addition to the mutual cooperation and pushing of the positioning convex block 1341 and the positioning groove 1351, the convex wall 1340 may also further push the second sliding block 135 to guarantee that the second sliding block 135 receives uniform vertical forces and may smoothly move.

In this embodiment, the transmission mechanism 136 is a screw rod arranged along the axial direction of the first clamping base 11. Two ends of the screw rod 136 are respectively fixed in cooperation holes 118 rotatably, axially corresponding to each other, of the first base portion 111 and the stopper 114. The screw rod 136 rotationally cooperates with the first sliding block 134, so that the first sliding block 134 may move axially along the first clamping base 11 when the screw rod is rotated. Of course, as another preferred embodiment of the present invention, the transmission mechanism 136 may also be a rope which passes through the instrument body 2 and the adapter 3 and connected to the first sliding block 134.

Further, in this embodiment, the first driving mechanism 133 further comprises a power source 137 which is arranged in the instrument body 2, passes through the adapter 3 and is connected to the transmission mechanism 136. The power source 137 is a rigid wire rope and is further connected to an operation handle 1371 at the proximal end of the instrument body 2.

To be specific, the first sliding block 134 and the second sliding block 135 are arranged on the sliding portions of the first clamping portion 113 and the second clamping portion 122 respectively in a penetrating manner, and are respectively provided with sliding grooves 1342 cooperating with the first sliding rod 115 and the second sliding rod 116, through holes 1343 in sliding fit with the third sliding rod 117, and penetration holes 1344 at the side adjacent to the first tying band buckle 1321 or the second tying band buckle 1322 for allowing the tying band 131 to pass through.

The first sliding block 134 is further provided with a threaded hole 1349 cooperating with the screw rod 136, so that the screw rod 136 may drive the first sliding block 134 to move along the axial direction when rotating.

Further, in order to prevent the tying band 131 at the position, where the tying band buckle 132 has moved, from dropping off, each of the first sliding block 134 and the second sliding block 135 is further provided with a limiting surface 1345 propped against the surfaces of the first sliding rod 115 and the second sliding rod 116 facing the cavity 110. The limiting surface 1345 is limited to the outer side of the tying band groove 1151 so as to limit the tying band 131 within the tying band groove 1151.

With reference to FIG. 5-11, in this embodiment, preferably, in order to cut off the unnecessary tying band 131 after the tubular tissue is gathered and tied into the pouch for facilitating the disengagement of the pouch-shaped tubular tissue, the tissue closure unit 1 in the present invention is further provided with a tying band cutting mechanism 16. There are two groups of tying band cutting mechanisms 16 respectively corresponding to portions, extending along the inner sides of the first clamping base 11 and the second clamping base 12, of the tying band 131. To be specific, in this embodiment, the two groups of tying band cutting mechanisms 16 are rotatably arranged in the first sliding block 134 and the second sliding block 135 respectively and located between the distal end of the penetration hole 1344 and the limiting surface 1345. Each of the first sliding block 134 and the second sliding block 135 is provided with an accommodation portion 1346 for accommodating the tying band cutting mechanism 16. The accommodation portion 1346 is communicated with the tying band groove 1151.

Each of the tying band cutting mechanisms 16 is provided with knife edges 161 opposite to the two tying bands 131 respectively and a guide portion 162 connected between the knife edges 161 to guide the rotation of the tying band cutting mechanism 16. As such, after the tubular tissue is tied into the pouch, the tying band cutting mechanism 16 is rotated through the cooperation of a driving element (such as the following knife head 171) and the guide portion 162, so that the knife edges 161 apply a force to the tying band 131 to cut off the unnecessary tying band 131.

In addition, in the present invention, the tissue closure unit 1 further comprises a cutting knife 17 for cutting off the pouch tubular tissue tied by the two groups of tying bands 131. A cutting knife triggering mechanism (not shown) for driving the cutting knife 17 to move towards the distal end is further arranged in the instrument body 2.

The cutting knife 17 may pass through the knife feeding groove 119 to stretch into the cavity 110 and to be located between the first tying band 1311 and the second tying band 1312. The cutting knife 17 is provided with a knife rod 170 and a knife head 171 protruding from the knife rod 170 towards the cavity 110. A knife edge 1710 for cutting through the tubular tissue is formed on the knife head 171. The end, away from the knife head 171, of the knife rod 170 passes through the adapter 3 and stretches into the instrument body 2. The cutting knife triggering mechanism is arranged in the instrument body 2 and cooperates with the proximal end of the knife rod 170.

In this embodiment, the cutting knife 17 adopts a single-sheet design, and is made of a material having certain flexibility and rigidity. The knife rod 170 and the knife head 171 are sheet-like and are integrally formed.

Preferably, the cutting knife 17 may also adopt a multi-sheet design, that is, the cutting knife 17 comprises at least two groups of the knife rods 170 and knife heads 171 which correspond to each other in the thickness direction thereof and are stacked together so as to cut through the tubular tissue together. As such, it is guaranteed that the cutting knife 17 not only has certain flexibility and thus may rotate by a certain angle when the tissue closure unit 1 may be rotationally arranged relative to the instrument body 2, as mentioned below, but also has certain rigidity and thus may cut through the tissue. Moreover, the knife heads 171 of the at least two knife edges 17 stacked together are staggered to a certain extent after rotating, so that the area of the knife edge 1710 is increased, and the cutting performance of the knife edge 1710 is further improved.

As another preferred embodiment of the present invention, the knife rod 170 and the knife head 171 of the cutting knife 17 may also be formed respectively and then are fixedly connected together by welding or other methods. At this time, the knife rod 170 may be made of a material having certain flexibility and rigidity, so that the knife rod is not only suitable for the situation that the tissue closure unit 1 may be rotationally arranged relative to the instrument body 2, as mentioned below, but also may effectively push and support the knife head 171 to cut through the tubular tissue. The knife head 171 is thus made of a material having relatively strong rigidity to guarantee the cutting effect. In the present invention, the knife head 171 is also used as a driving element of the tying band cutting mechanism 16. Thus, further, each of the first sliding block 134 and the second sliding block 135 is further provided with a slit 1347 for allowing the cutting knife 17 to stretch into the accommodation portion 1346. When the cutting knife triggering mechanism drives the cutting knife 17 to move towards the distal end, the cutting knife 17 may pass through the slit 1347 to stretch into the accommodation portion 1346, and cooperates with the guide portion 162 to enable the tying band cutting mechanism 16 to rotate, and thus the knife edge 161 stretches into the tying band groove 1151 to cut off the tying band 131.

To be specific, the knife head 171 is triangular. The knife edges 1710 are formed at the head and upper and lower sides of the distal end of the knife head 171. A guide inclined surface 1620 for cooperating with the knife edge 1710 is formed on the guide portion 162, so that when the knife head 171 stretches into the accommodation portion 1346, the knife edge 1710 moves along the guide inclined surface 1620 to push the tying band cutting mechanism 16 to rotate.

It can be seen from the above description in conjunction with FIGS. 1-11 that when the tissue closure device in this embodiment stretches into the human body for use:

firstly, the pushing element drives the driving ring 15 to move towards the proximal end and then the second clamping base 12 is opened under the action of the elastic element 14, and thus the tubular tissue is accommodated in the cavity 110;

secondly, the transmission mechanism 136 is driven to drive the first sliding block 134 and push the first tying band buckle 1321 to move towards the proximal end along the tying band 131 to the first position, then second clamping base 12 is closed by pushing the driving ring 15 by the pushing element, that is, the second clamping base 12 and the first clamping base 11 are closed, and at this position, the two groups of the tying band buckles 132 are mutually buckled, and the first sliding block 134 and second sliding block 135 are also positioned mutually;

thirdly, the transmission mechanism 136 drives the first sliding block 134 and the second sliding block 135, and thus pushes the first tying band buckle 1321 and the second tying band buckle 1322 to synchronously move from the distal end to the proximal end relative to the tying band 131 so as to gather the tubular tissue into a pouch; and finally, after the tubular tissue is gathered, the cutting knife triggering mechanism is driven, so that the cutting knife 17 stretches into the cavity 110 to cut through the pouch-shaped tubular tissue tied by the two tying bands 131, and at the same time, the cutting knife 17 drives the tying band cutting mechanism 16 to cut off the unnecessary tying band 131. At this time, the second clamping base 12 may be opened, and the pouch-shaped tubular tissue needed to be removed is taken out. When the pouch-shaped tubular tissue is taken out, the T-shaped positioning structure 13151 connected to the outer side of the connection portion 1315, at the proximal end of the tying band 131 may be disconnected by applying a force, so that the tying band 131 disengages from the first base portion 111.

Further, after the operation of the cutting knife 17 and the tying band cutting mechanism 16 is completed, the first sliding block 134 and the second sliding block 135 may be driven to move towards the distal end through the transmission mechanism 136, and then keep away from the pouch-shaped tubular tissue, thereby further facilitating taking out of the pouch-shaped tubular tissue.

As mentioned above, in the above preferred embodiment of the present invention, the tying band buckle 132 may be driven to move towards the proximal end by the first driving mechanism 133 and then cooperates with the tying band 131 to tie the tubular tissue into the pouch. Indeed, as another preferred embodiment of the present invention, with reference to FIG. 13, the proximal end of the tying band 131 may gradually move towards the distal end and the tying band buckle 132 cooperates with the tying band 131 to tie the accommodated tubular tissue into the pouch.

To be specific, in the another preferred embodiment, the first free end 1313 and the second free end 1314 of the tying band 131 extend respectively from the proximal end to the distal end and are then reversely bent to extend from the distal ends of the first clamping base 11 and the second clamping base 12. A basic shaft 120 for allowing the tying band 131 to move from the distal end to the proximal end is arranged at the distal end of each of the first clamping base 11 and the second clamping base 12. The first driving mechanism 133 is a pulling band which passes through the first clamping base 11 and the second clamping base 12 from the proximal end and is fixed to the first free end 1313 and the second free end 1314.

Figure 14:
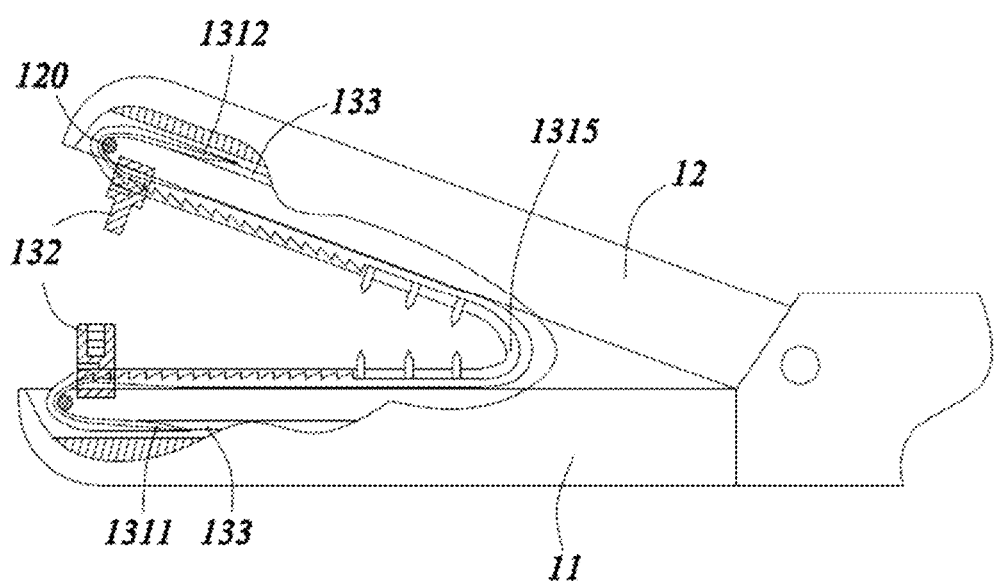
FIG. 14 is a partial stereoscopic sectional view of another preferred embodiment of the tissue closure device of the present invention.

It can be seen from FIG. 14 that by pulling the pulling band 133, the first free end 1313 and the second free end 1314 of the tying band 131 move from the distal end to the proximal end. The connection portion 1315 of the tying band 131 moves from the proximal end to the distal end, and the tying band 131 and the tying band buckle 132 together gather the tubular tissue into the pouch. In this case, it may also be regarded as that the tying band buckle 132 moves synchronously relative to the tying band 131 and cooperates with the tying band 131 to gather the tubular tissue.

Thus, it can be seen from all the above embodiments that when the tissue closure device of the present invention is used, it only requires that the lower and upper tying band buckles 132 synchronously move relative to the tying band 131 (comprising the case that the tying band buckles 132 synchronously move along the tying band 131 or two sides of the tying band 131 moves synchronously in the tying band buckles 132 in a penetrating manner) and cooperate with each other to shrink the cavity 110 and thus gather the tubular tissue.

In addition, in the present invention, the tissue closure device may be a linearly-operated medical instrument, that is, the instrument body 2 and the tissue closure unit 1 are directly connected into a straight line through the adapter 3 and arranged coaxially. However, in order to enable the tissue closure device of the present invention to cooperate with the closure operation of tubular tissues in different states, in this embodiment, as shown in FIGS. 1-5, in the tissue closure device, the tissue closure unit 1 is arranged to be rotatable relative to the instrument body 2 through the adapter 3, so that the tissue closure unit 1 may rotate by 90 degrees relative to the instrument body 2, and thus the tissue closure device of the present invention may enter the relatively deep pelvic floor position for operation. Moreover, the tissue closure device is simple in operation and convenient to use and reduces the surgery cost.

To be specific, the instrument body 2 is provided with a main body 21 and a first connection mechanism 22 arranged at the distal end of the main body 21. The tissue closure unit 1 is provided with a second connection mechanism arranged at the proximal end. In this embodiment, the second connection mechanism is the above pair of lugs 112 protruding from the first base portion 111 towards the adapter 3. In addition, the first connection mechanism 22 is also arranged as a pair of lugs protruding towards the adapter 3, and a make-way space 24 for making way for the adapter 3 when the tissue closure unit 1 is driven to rotate is formed between the lugs 112, 22.

The adapter 3 is connected between the instrument body 2 and the tissue closure unit 1, that is, the adapter 3 is formed as a connection joint of the instrument body 2 and the tissue closure unit 1. The adapter 3 is provided with an adapter body 31, a pair of first ear portions 32 protruding from two opposite sides of the adapter body 31 towards the instrument body 2 and a pair of second ear portions 33 protruding from the two opposite sides of the adapter body 31 towards the tissue closure unit 1. The first ear portion 32 rotationally cooperates with the first connection mechanism 22 through a pivot shaft (not shown), and the second ear portion 33 cooperates with the second connection mechanism 112 through a pivot shaft (not shown). The first ear portion 32 and the second ear portion 33 are aligned with each other and symmetrically arranged along the axial direction of the adapter 3.

Of course, the tissue closure device further comprises a driving element 4 for driving the tissue closure unit 1 to rotate. The driving element 4 passes through the instrument body 2 and the adapter 3 from the proximal end and is fixed o the tissue closure unit 1. The fixing position of the driving element 4 on the tissue closure unit 1 is located between the second ear portions 33 and deviates from the axis of the tissue closure unit 1.

In addition, in order to facilitating the tissue closure device of the present invention stretching into the tissue without damaging the tissue, the outer diameter of the adapter 3 is the same as the outer diameter at the first connection mechanism 22 and the second connection mechanism 112, and the tissue closure device is further provided with a sleeve (not shown) arranged at the outer side of the adapter 3. The sleeve may be the above push-pull element for driving the driving ring 15 to move axially along the tissue closure unit 1.

In this embodiment, the driving element 4 is a pull rope; and a pull rope hole 311 is arranged at a position, corresponding to the above fixing position, of the adapter body 31. In addition, a pair of driving elements 4 is arranged symmetrically along the radial direction, so that the tissue closure unit 1 may rotate towards two opposite directions relative to the instrument body 2 under the respective driving of the pair of the driving elements 4, thus can adapt different environments.

Further, for facilitating limiting the rotating angle of the tissue closure unit 1, a limiting structure 23 for limiting the rotating angle of the first ear portion 32 or the second ear portion 33 is arranged on each of the first connection mechanism 22 and the second connection mechanism 112 and at each of two sides of the pivot shaft. In the present invention, an included angle between limiting structures 23 at two sides of the pivot shaft is designed to be 90 degrees and the limiting structures 23 and the rotating shaft are equidistantly arranged, so that the tissue closure unit 1 may rotate by 90 degrees relative to the instrument body 2 under the action of the driving element 4.

To be specific, a recess portion 221 for accommodating the first ear portion 32 or the second ear portion 33 is arranged on each of the first connection mechanism 22 and the second connection mechanism 112. The connection position of the pivot shaft is located at the intermediate position of the recess portion 221. Inner wall surfaces, located at two sides of the pivot shaft, of the recess portion 221 are formed as the limiting structures 23.

Preferably, the tail end of each of the first ear portion 32 and the second ear portion 33 is arcuate. The inner wall surface, between the limiting structures 23, of the recess portion 221 is also arcuate.

In addition, for facilitating the arrangement of the above cutting knife 17 and the power source 137 of the screw rod 136, the adapter 31 is further provided with a knife groove 312 and a steel wire rope hole 313 for allowing the cutting knife 17 and the power source 137 to pass through respectively. The knife groove 312 extends between the pair of first ear portions 32. The steel wire rope hole 313 is adjacent to the knife groove 312.

It should be understood that although the description is described based on the embodiments, and not every embodiment includes only one independent technical solution. This presentation manner of the description is only for clarity. Those skilled in the art should consider the description as a whole, and technical solutions in all of the embodiments may also be properly combined to form other embodiments that will be understood by those skilled in the art.

The above detailed description only aims to specifically illustrate the feasible embodiments of the present invention, and is not intended to limit the scope of protection of the present invention. Equivalent embodiments or modifications thereof made without departing from the spirit of the present invention shall fall within the protection scope of the present invention.

What is claimed is:

1. A tissue closure device, comprising:
   a first clamping base and a second clamping base which may be opened and closed oppositely and form a cavity therebetween for accommodating a tubular tissue when being closed; and
   a pouch assembly arranged to cooperate with the first clamping base and the second clamping base, wherein the pouch assembly comprises:
   a tying band which extends along a side, facing the cavity, of each of the first clamping base and the second clamping base, and is provided with a first free end located at a distal end of the first clamping base and a second free end located at a distal end of the second clamping base;
   a first tying band buckle which is slidably arranged on the tying band in a penetrating manner and arranged adjacent to the first free end in an initial state;
   a second tying band buckle which is slidably arranged on the tying band in a penetrating manner and arranged adjacent to the second free end in an initial state, wherein the second tying band buckle is opposite to the first tying band buckle and is configured to be buckled with the first tying band buckle after the tubular tissue is accommodated in the cavity and the first clamping base and the second clamping base are closed; and
   a first driving mechanism which enables the first tying band buckle and the second tying band buckle to move synchronously relative to the tying band after the first tying band buckle and the second tying band buckle are buckled and then cooperate with the tying band to gather the tubular tissue into a pouch.

2. The tissue closure device according to claim 1, wherein the first driving mechanism comprises:
   a first sliding block which is arranged on the first clamping base in a sliding manner along an axial direction of the first clamping base and is abutted against the side, facing the first free end, of the first tying band;
   a second sliding block which is arranged on the second clamping base in a sliding manner along an axial direction of the second clamping base and is abutted against the side, facing the second free end, of the second tying band; and
   a transmission mechanism arranged to cooperate with the first sliding block, wherein when the tissue closure device is in an initial state, the first sliding block and the second sliding block are respectively located at distal ends of the first clamping base and the second clamping base, and the first tying band buckle and the second tying band buckle are staggered; after the first clamping base and the second clamping base are oppositely opened to accommodate the tubular tissue in the cavity, the transmission mechanism drives the first sliding block to move towards a proximal end to a first position, then the first clamping base and the second clamping base are closed, the first tying band buckle and the second tying band buckle are buckled together, and the first sliding block and the second sliding block are mutually positioned, and finally, the transmission mechanism continuously drives the first sliding block and the second sliding block to move towards the proximal end at the same time, so that the tubular tissue is gathered towards the proximal end to form a pouch.

3. The tissue closure device according to claim 2, wherein the tying band comprises a first tying band and a second tying band arranged at an interval side by side along a radial direction; the pouch assembly comprises two groups of first tying band buckles and second tying band buckles corresponding to the first tying band and the second tying band respectively; the first sliding block is abutted against and cooperates with two first tying band buckles at the same time; and the second sliding block is abutted against and cooperates with two second tying band buckles at the same time.

4. The tissue closure device according to claim 3, wherein each of the first clamping base and the second clamping base is provided with a first sliding rod and a second sliding rod which are arranged at an interval in the radial direction and correspond to the first tying band and the second tying band respectively; a tying band groove for positioning the tying band is recessed at the side, facing the cavity, of each of the first sliding rod and the second sliding rod; the first sliding block and the second sliding block are arranged on the first sliding rod and the second sliding rod in a penetrating manner respectively, and are respectively provided with perforation holes for allowing the tying band to pass through, at a side adjacent to the first tying band buckle or the second tying band buckle; each of the first sliding block and the second sliding block is further provided with a limiting surface propped against surfaces of the first sliding rod and the second sliding rod facing the cavity; and the limiting surface is limited to an outer side of the tying band groove so as to limit the tying band within the tying band groove.

5. The tissue closure device according to claim 3, wherein the tissue closure device further comprises:
   a cutting knife arranged on the first clamping base, located between the first tying band and the second tying band and provided with a knife head protruding towards the cavity; and
   a cutting knife triggering mechanism configured to drive the cutting knife to move towards the distal end to cut through the tubular tissue between the first tying band and the second tying band when portions, corresponding to the first tying band and the second tying band respectively, of the tubular tissue are gathered to form the pouch.

6. The tissue closure device according to claim 5, wherein the tissue closure device further comprises:
   a tying band cutting mechanism rotatably arranged in the first sliding block and the second sliding block and provided with a knife edge opposite to the tying band and a guide portion corresponding to the cutting knife axially,
   wherein each of the first sliding block and the second sliding block is provided with an accommodation portion for accommodating the tying band cutting mechanism and a slit for allowing the cutting knife to stretch into the accommodation portion; the accommodation portion is communicated with the tying band groove; and when a cutting knife triggering mechanism drives the cutting knife to move towards a distal end, the cutting knife passes through the slit, stretches into the accommodation portion and cooperates with the guide portion to rotate the tying band cutting mechanism, whereupon the knife edge applies a force to the tying band to cut off the tying band.

7. The tissue closure device according to claim 5, wherein the cutting knife is further provided with a knife rod connected to the distal end of the knife head; both the knife rod and the knife head are sheet-like and are integrally formed; the cutting knife is in a single-sheet arrangement or multi-sheet arrangement; when the cutting knife is in the multi-sheet arrangement, the cutting knife comprises at least two groups of the knife rods and knife heads which correspond to each other and are stacked together along a thickness direction of the cutting knife to cut through the tubular tissue together.

8. The tissue closure device according to claim 1, wherein the first free end and the second free end of the tying band extend from a proximal end to a distal end and are then reversely bent to extend around basic shafts arranged on the first clamping base and the second clamping base from the distal ends of the first clamping base and the second clamping base respectively; and the first driving mechanism is a pulling band which passes through the first clamping base and the second clamping base from the proximal end and is fixed to the first free end and the second free end.

9. The tissue closure device according to claim 1, wherein the tying band is bent to be U-shaped and is provided with a connection portion located at a proximal end, main body portions connected between the connection portion and the first free end as well as the second free end, and a thorn protruding from the connection portion and/or a position adjacent to the connection portion, of the main body portion into the cavity.

10. The tissue closure device according to claim 9, wherein the thorn protrudes from an intermediate position of the connection portion into the cavity.

11. The tissue closure device according to claim 9, wherein a first ratchet for unidirectionally and cooperatively sliding with the first tying band buckle or the second tying band buckle is arranged at a side, facing the cavity, of the main body portions; each of the first tying band buckle and the second tying band buckle is provided with a sleeve portion slidably sleeving the tying band, a restriction portion protruding from the sleeve portion towards one side of the cavity, and a positioning buckle connected to a lower side of the sleeve portion; and the restriction portion is provided with a second ratchet unidirectionally cooperating with the first ratchet.

12. The tissue closure device according to claim 1, comprising:
an instrument body provided with a main body and a first connection mechanism arranged at a distal end of the main body;
a tissue closure unit which is provided with a second connection mechanism arranged at a proximal end and on which the first clamping base, the second clamping base and the pouch assembly are arranged, and
an adapter which is connected between the instrument body and the tissue closure unit and is provided with an adapter body, a pair of first ear portions protruding from two sides of the adapter body towards the instrument body and a pair of second ear portions protruding from the two sides of the adapter body towards the tissue closure unit, wherein the first ear portions rotationally cooperate with the first connection mechanism through a pivot shaft, the second ear portions cooperate with the second connection mechanism through a pivot shaft, and the first ear portions and the second ear portions are aligned with each other along an axial direction of the adapter; and
a driving element which passes through the instrument body and the adapter and is fixed to the tissue closure unit, wherein a fixing position of the driving element on the tissue closure unit is located between the second ear portions and deviates from an axis of the tissue closure unit.

13. The tissue closure device according to claim 12, wherein a limiting structures for limiting a rotating angle of the first ear portions or the second ear portions are arranged on each of the first connection mechanism and the second connection mechanism and at each of two sides of the pivot shafts.

14. The tissue closure device according to claim 13, wherein a recess portions for accommodating the first ear portion or the second ear portions is arranged on each of the first connection mechanism and the second connection mechanism; a connection position of the pivot shaft is located at an intermediate position of the recess portion; and inner wall surfaces, located at two sides of the pivot shafts, of the recess portion are formed as the limiting structures.

15. The tissue closure device according to claim 12, wherein each of the first connection mechanism and the second connection mechanism is a pair of lugs protruding towards the adapter; and a make-way space for making way for the adapter body when the tissue closure unit is driven to rotate is formed between the lugs.

16. The tissue closure device according to claim 12, wherein an outer diameter of the adapter is the same as an outer diameter at the first connection mechanism and the second connection mechanism, and the tissue closure device is further provided with a sleeve arranged at an outer side of the adapter.

* * * * *